(12) United States Patent
Pahan

(10) Patent No.: US 11,020,366 B2
(45) Date of Patent: **\*Jun. 1, 2021**

(54) LOCOMOTOR ACTIVITY AND INCREASE IN LONGEVITY OF LATE INFANTILE NEURONAL CERIOD LIPOFUSCINOSIS SUBJECTS BY GEMFIBROZIL

(71) Applicant: Rush University Medical Center, Chicago, IL (US)

(72) Inventor: Kalipada Pahan, Skokie, IL (US)

(\*) Notice: Subject to any disclaimer, the term of this patent is extended or adjusted under 35 U.S.C. 154(b) by 0 days.

This patent is subject to a terminal disclaimer.

(21) Appl. No.: 16/472,638

(22) PCT Filed: Dec. 28, 2017

(86) PCT No.: PCT/US2017/068699
§ 371 (c)(1),
(2) Date: Jun. 21, 2019

(87) PCT Pub. No.: WO2018/126000
PCT Pub. Date: Jul. 5, 2018

(65) Prior Publication Data
US 2019/0358188 A1 Nov. 28, 2019

Related U.S. Application Data

(60) Provisional application No. 62/440,305, filed on Dec. 29, 2016.

(51) Int. Cl.
*A61K 31/216* (2006.01)
*A61P 25/28* (2006.01)

(52) U.S. Cl.
CPC ............ *A61K 31/216* (2013.01); *A61P 25/28* (2018.01)

(58) Field of Classification Search
CPC .................................................... A61K 31/216
See application file for complete search history.

(56) References Cited

U.S. PATENT DOCUMENTS 9,750,712 B2 \* 9/2017 Pahan ................. A61K 31/192

FOREIGN PATENT DOCUMENTS

WO WO2014089449 \* 6/2014

OTHER PUBLICATIONS

Lupp et al. CAS: 149,215657, 2008.\*
Amelie Lupp, et al., Ciprofibrate, Clofibric Acid and Respective Glycinate Derivatives, Lipid Regulating Agents, Arzneim-ForschDrugRes (Drug REsearch) 2008, pp. 225-241.
K. Wang, Molecular Mechanisms of Hepatic Apoptosis, Cell Death and Disease, 2014, pp. 1-10.
Nicholas D. Mazarakis, et al., Apoptosis in Neural Development and Disease, Archives of Disease in Childhood, 1997, pp. F165-170.

\* cited by examiner

*Primary Examiner* — Rei Tsang Shiao
(74) *Attorney, Agent, or Firm* — Taft Stettinius & Hollister LLP; Joseph M. Bennett-Paris

(57) ABSTRACT

Provided herein are methods for treatment of a neurodegenerative disease, such as Late Infantile Neuronal Ceroid Lipofuscinosis, including administering to a subject in need of such treatment a composition comprising a therapeutically effective amount of an agent comprising a fibrate.

15 Claims, 8 Drawing Sheets

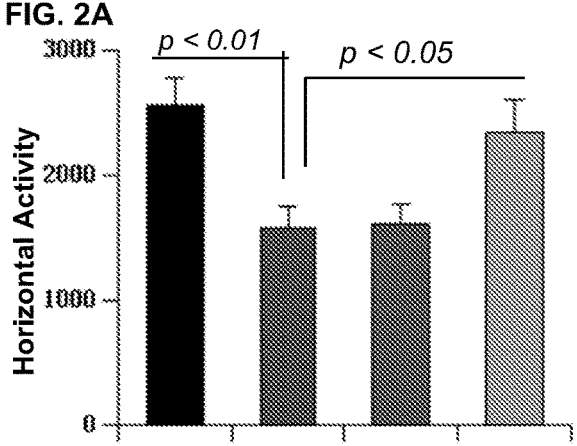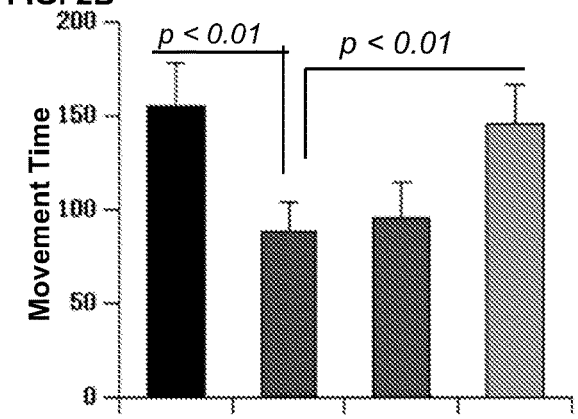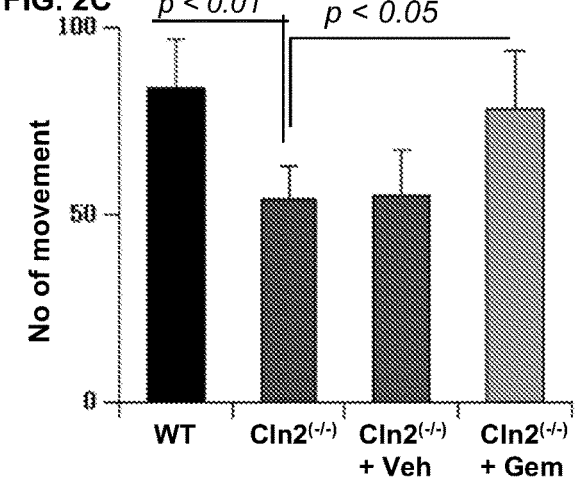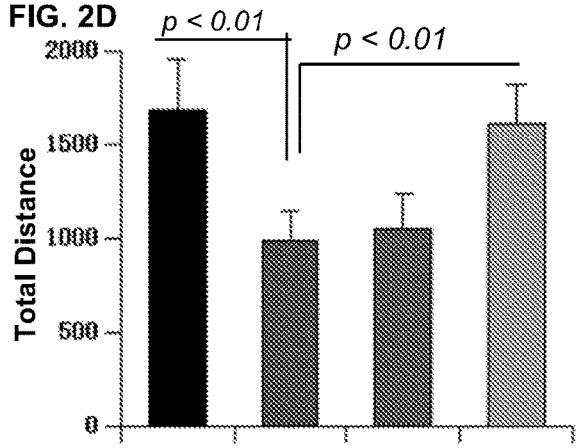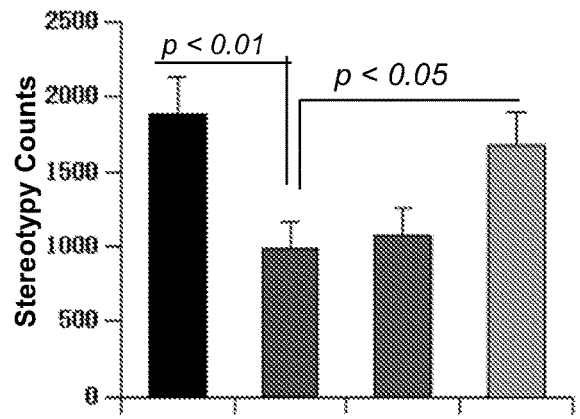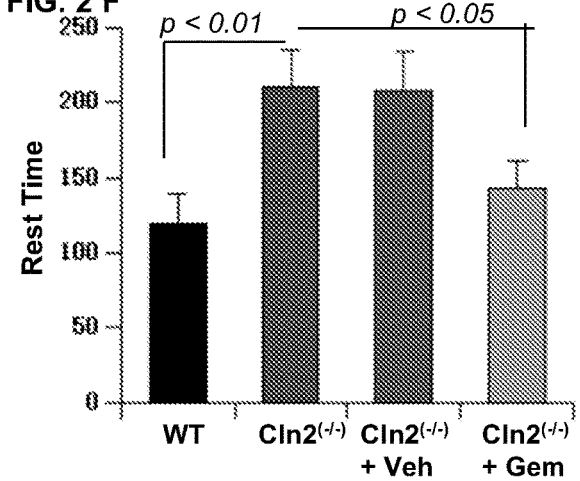

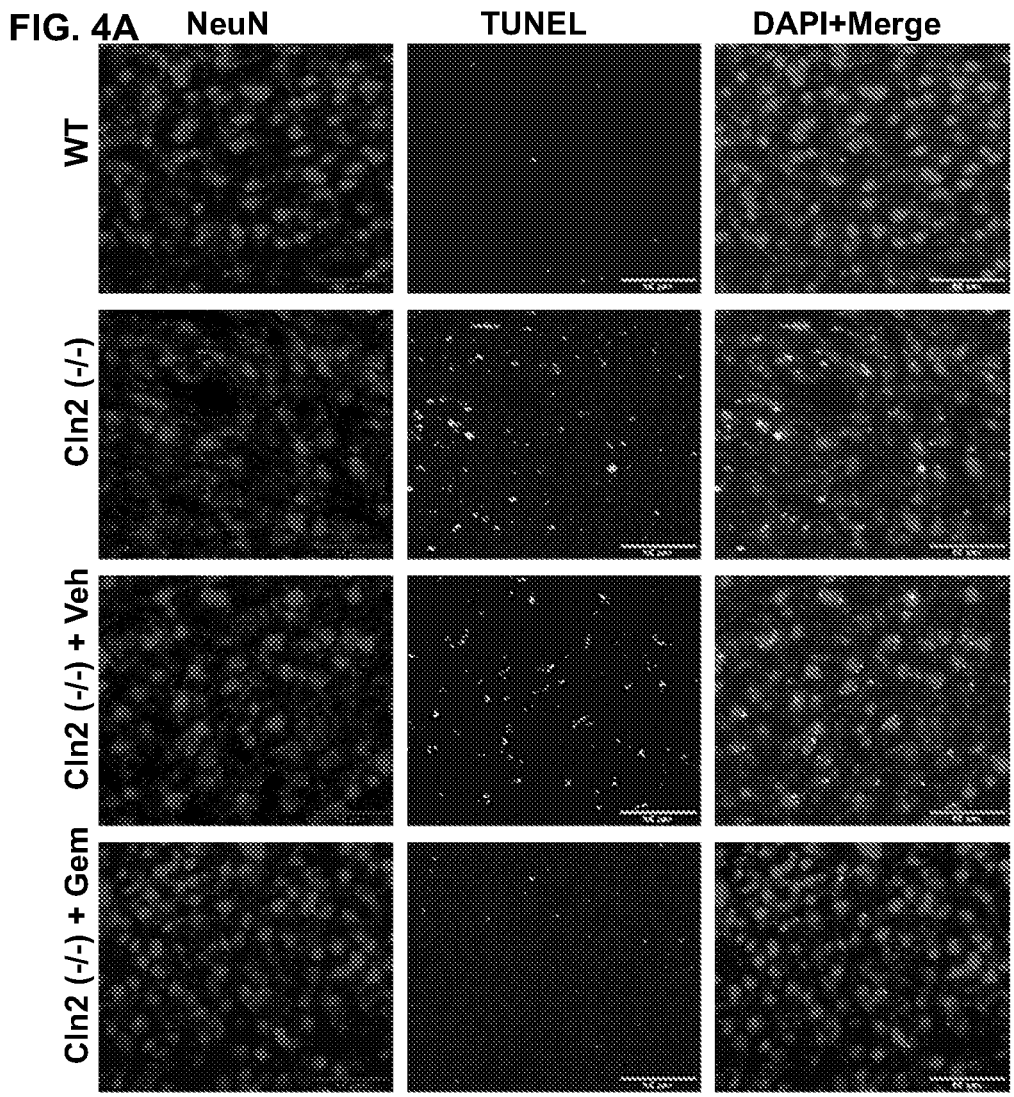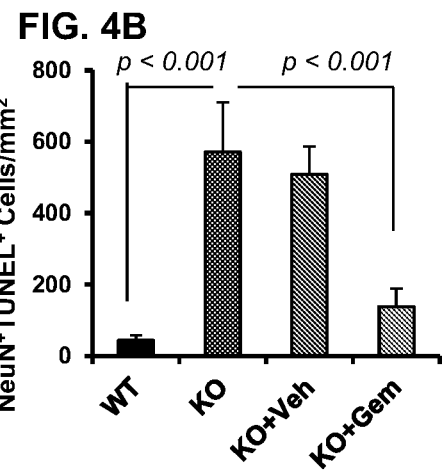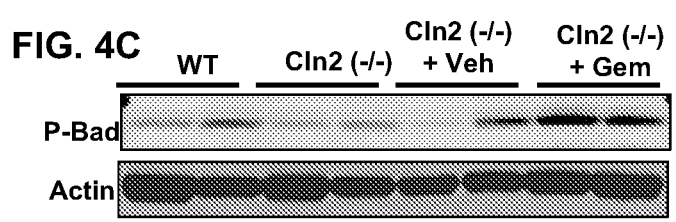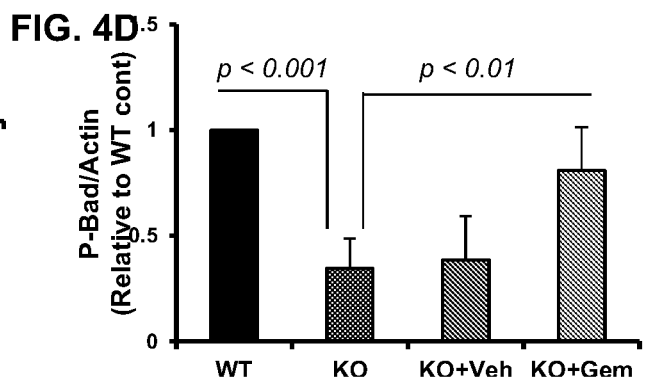

FIG. 6A Motor cortex
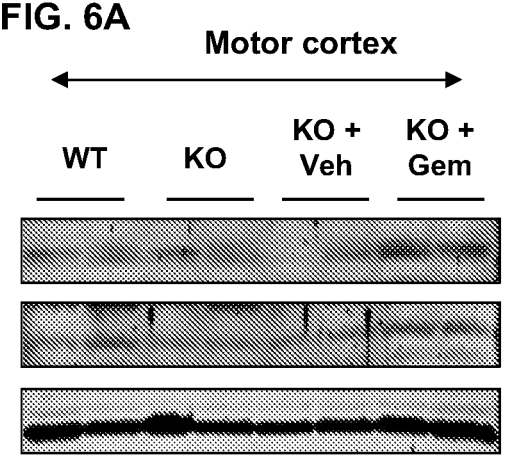
FIG. 6D Striatum
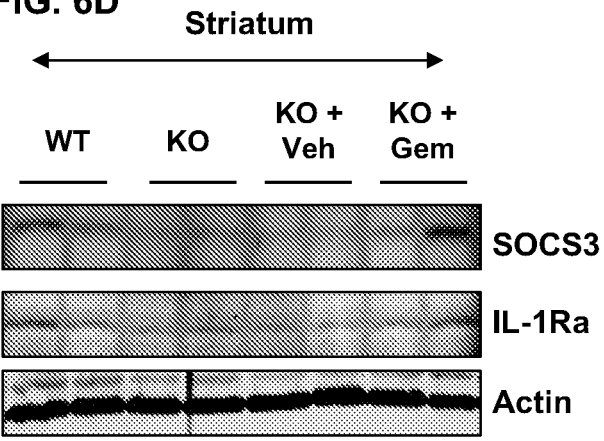
FIG. 6B
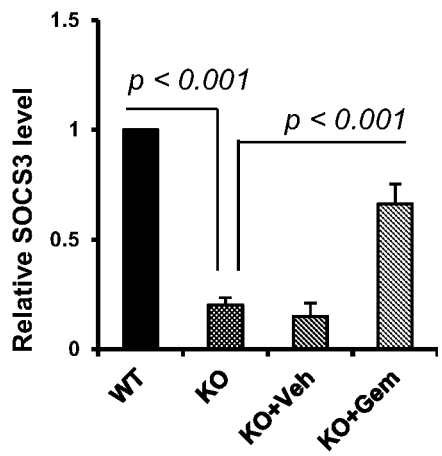
FIG. 6E
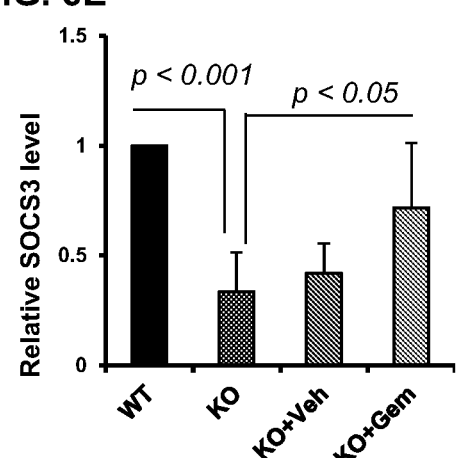
FIG. 6C
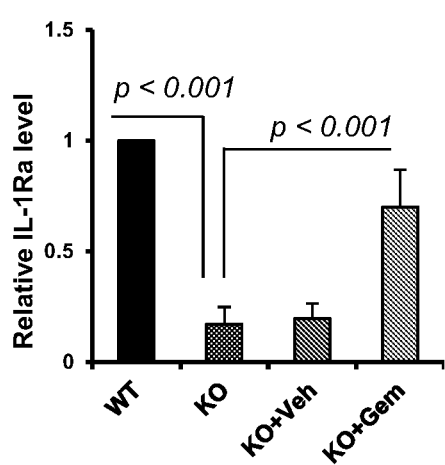
FIG. 6F
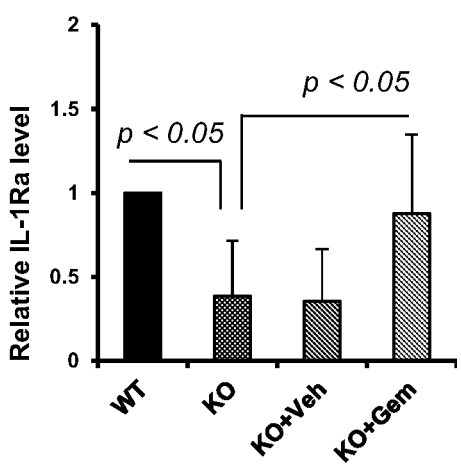

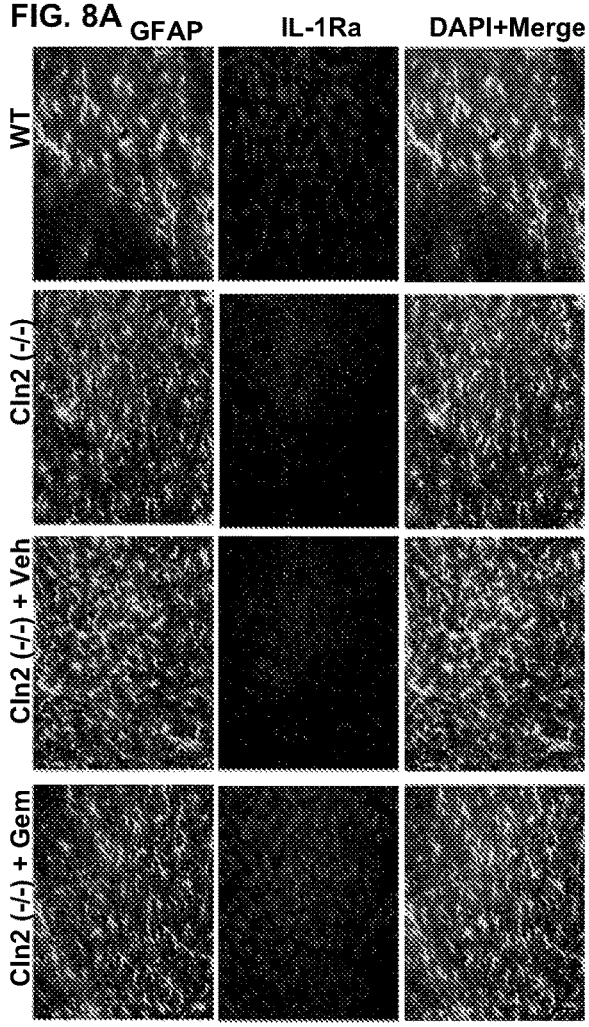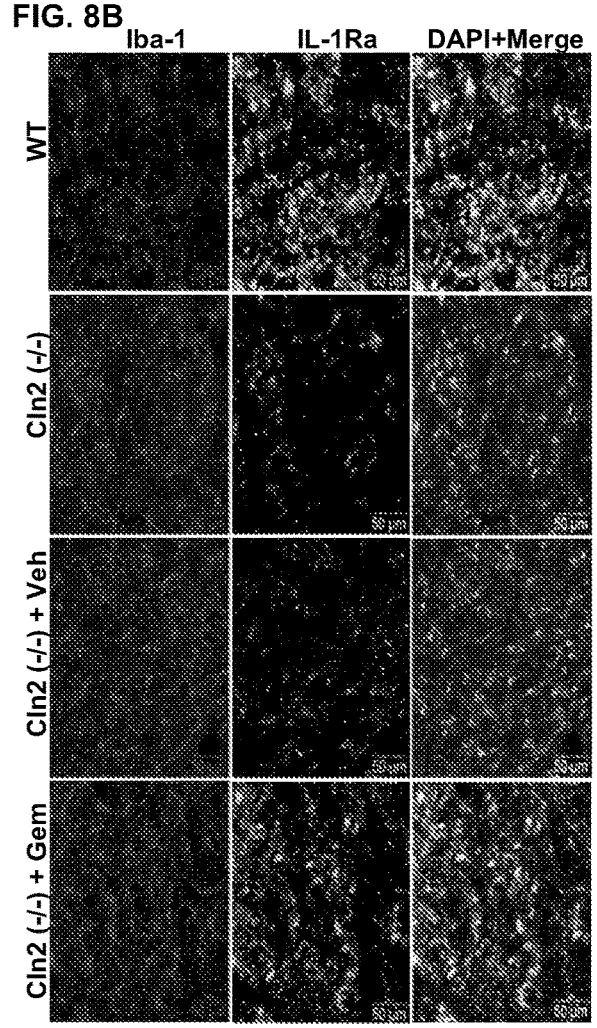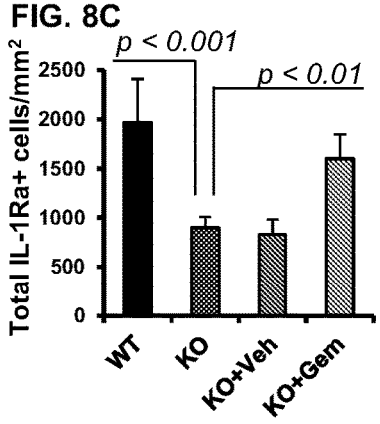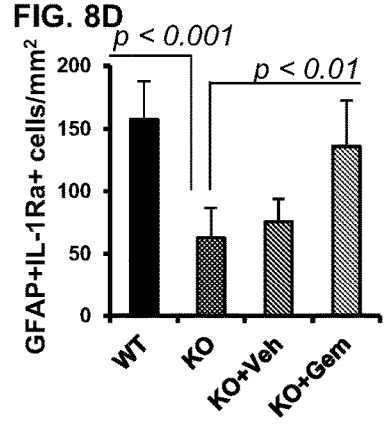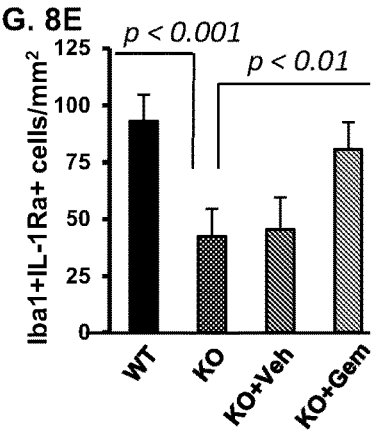

LOCOMOTOR ACTIVITY AND INCREASE IN LONGEVITY OF LATE INFANTILE NEURONAL CERIOD LIPOFUSCINOSIS SUBJECTS BY GEMFIBROZIL

RELATED APPLICATIONS

This application claims the benefit under 35 U.S.C. § 371 of International Application No. PCT/US2017/068699, filed Dec. 28, 2017, which claims the benefit of U.S. Provisional Application No. 62/440,305, filed Dec. 29, 2016; which are incorporated by reference herein in their entirety.

TECHNICAL FIELD

The present invention relates to methods for treating a neurodegenerative disease, such as Late Infantile Neuronal Ceroid Lipofuscinosis.

BACKGROUND

Lysosomes are membrane bound organelles containing several acid hydrolases that are responsible for degradation of lipid, protein, carbohydrates, and nucleic acids (De Duve & Wattiaux 1966). Defects/deficiencies in almost any of them results in accumulation of undigested/partially digested material in the lysosomes and forms the basis of numerous lysosomal storage disorders (LSDs) (De Duve & Wattiaux 1966, Perez-Sala et al. 2009). Late Infantile Neuronal Ceroid Lipofuscinosis (Jansky-Bielschowsky disease, LINCL, Type 2) is one form of NCL that is caused by too mutations in the Cln2 gene. These mutations lead to deficiency and/or loss of function of tripeptidyl tripeptidase I (TPP-I, a 46 kDa pepstatin insensitive lysosomal protease), resulting in the accumulation of autofluorescent materials in the brain (Sleat et al. 1997, Lane et al. 1996). LINCL typically produces symptoms at the age of 2-4 years, progresses rapidly and ends in death between ages 8 to 10 as a result of a dramatic decrease in the number of neurons and other cells (Lane et al. 1996, Sleat et al. 1997). Therefore, increasing life span and/or improving the quality of life in patients with LINCL or other NCLs are an important area of research. However, despite years of investigations, only one treatment is available for this disease, especially LINCL; all approaches are merely supportive or symptomatic, indicating an urgent need for novel therapeutic approaches (Chang et al. 2008).

Several studies conclude that neuro-inflammation and induction of apoptotic pathways can be attributed to the neuronal damage in most forms of NCL, including LINCL (Geraets et al. 2016, Dhar et al. 2002, Puranam et al. 1997, Kohan et al. 2011). Although inflammation is not the initiating factor in LINCL, glia-mediated sustained inflammatory response is believed to contribute to disease progression (Cooper et al. 2015, Macauley et al. 2014). Gemfibrozil (gem), an FDA-approved lipid-lowering drug, is known to reduce the level of triglycerides in the blood circulation and decrease the risk of hyperlipidemia (Robins et al. 2001, Rubins & Robins 1992, Rubins et al. 1999). However, a number of recent studies from us and others reveal that apart from its lipid-lowering effects, gem can also regulate many other signaling pathways responsible for inflammation, switching of T-helper cells, cell-to-cell contact, migration, oxidative stress, and lysosomal biogenesis (Ghosh & Pahan 2012a, Corbett et al. 2012, Ghosh et al. 2012, Jana et al. 2007, Jana & Pahan 2012, Dasgupta et al. 2007, Pahan et al. 2002, Roy & Pahan 2009, Ghosh et al. 2015).

Here, we investigated the therapeutic efficacy of gem in mouse model of LINCL. Behavioral analysis and survival studies on Cln2$^{(-/-)}$ mice showed increased longevity and improvement of motor behavior in gem-treated animals compared to vehicle (0.1% methyl cellulose)-treated controls. The burden of storage materials and neuronal apoptosis were also found to be partially reduced in gem-treated animals with increase in levels of phospho-BCL2 Associated Agonist Of Cell Death (P-BAD), an anti-apoptotic molecule. Furthermore, levels of anti-inflammatory factors like suppressor of cytokine signaling 3 (SOCS3) and Interleukin-1 receptor antagonist (IL-1Ra) was found to be elevated in gem-treated animals. Taken together, this study indicates a neuroprotective role of gem in Cln2$^{(-/-)}$ animals.

SUMMARY

Provided herein are methods for treatment of a neurodegenerative disease. The neurodegenerative disease may be neuronal ceroid lipofuscinosis, Alzheimer's disease, Huntington's disease, Amyotrophic lateral sclerosis (ALS), Parkinson's disease, including Parkinson's plus diseases such as multiple system atrophy (MSA), progressive supranuclear palsy (PSP), corticobasal degeneration (CBD) or dementia with Lewy bodies (DLB). Batten disease is the most common form of a group of disorders called the neuronal ceroid lipofuscinosis (NCL). The (NCL) may be infantile NCL (INCL, Santavuori-Haltia Disease), Late Infantile Neuronal Ceroid Lipofuscinosis (LINCL), juvenile NCL (JNCL), or adult NCL (ANCL). The neurodegenerative disease may be caused by a lysosomal storage disorder. The lysosomal storage disorder may be, for example, Tay-Sach's disease, Fabry disease, Niemann-Pick disease, Gaucher disease, Hunter Syndrome, Alpha-mannosidosis, Aspartylglucosaminuria, Cholesteryl ester storage disease, Chronic Hexosaminidase A Deficiency, Cystinosis, Danon disease, Farber disease, Fucosidosis, or Galactosialidosis.

The method may comprise administering to a subject in need of such treatment a composition comprising a therapeutically effective amount of an agent comprising a fibrate. The fibrate may be gemfibrozil, fenofibrate, clofibrate, bezafibrate, ciprofibrate or clinofibrate.

Also provided herein is a method of decreasing neuronal apoptotic cell death in a subject having a neurodegenerative disease. The method includes administering to the subject a composition comprising a therapeutically effective amount of an agent that decreases neuronal apoptotic cell death, where the agent comprises a fibrate.

Further provided herein is a method of prolonging a lifespan of a subject having a neurodegenerative disease. The method includes administering to the subject a composition comprising a therapeutically effective amount of an agent that prolonging a lifespan of a subject having a neurodegenerative disease, where the agent comprises a fibrate.

Also provided herein is a method of improving motor behavior in a subject having a neurodegenerative disease. The method includes administering to the subject a composition comprising a therapeutically effective amount of an agent that improving motor behavior, where the agent comprises a fibrate.

Also provided herein is a method of increasing levels of anti-inflammatory factors in a brain of a subject having Late Infantile Neuronal Ceroid Lipofuscinosis. The method includes administering to the subject a composition comprising a therapeutically effective amount of an agent that that increases levels of anti-inflammatory factors in a brain of the subject having the Late Infantile Neuronal Ceroid Lipofuscinosis relative to a control not receiving the agent, where the agent comprises a fibrate.

BRIEF DESCRIPTION OF THE DRAWINGS

FIG. 2A-2F. Gem treatment delays the loss of motor activity in $Cln2^{(-/-)}$ mice: $Cln2^{(-/-)}$ animals (4 weeks old) were treated with gem (dissolved in 0.1% MeC) orally at a dose of 7.5 mg/kg body weight/day. After 8 weeks of treatment, mice were monitored for horizontal activity (2A), movement time (2B), number of movement (2C), total distance travelled (2D), stereotypy counts (2E), and rest time (2F). $Cln2^{(-/-)}$ mice receiving only vehicle and background-matched wild type (WT) mice were also run for comparison. Results represent mean±SEM of twelve mice (n=12) per group. Male and female mice were kept in each group in equal ratio.

FIG. 4A-4D. Gem treatment attenuates apoptosis in vivo in the motor cortex of $Cln2^{(-/-)}$ mice: $Cln2^{(-/-)}$ animals (4 weeks old) were treated with gem (dissolved in 0.1% MeC) orally at a dose of 7.5 mg/kg body weight/day. After 8 weeks of treatment, cortical sections (immediately dorsal to CA1 hippocampal region) were double-labeled for NeuN and TUNEL (4A). NeuN$^+$TUNEL$^+$ cells were counted (4B) in two different cortical sections of each of six different mice (n=6) per group. 4C) Cortical homogenates were immunoblotted for phospho-BAD. Actin was run as loading control. 4D) Bands were scanned and values (P-BAD/Actin) are presented as relative to WT control. Results are mean±SEM of four mice per group.

FIGS. 6A-6F. Gem treatment upregulates the expression of anti-inflammatory molecules in vivo in the CNS of $Cln2^{(-/-)}$ mice: $Cln2^{(-/-)}$ animals (4 weeks old) were treated with gem (dissolved in 0.1% MeC) orally at a dose of 7.5 mg/kg body weight/day. After 8 weeks of treatment, the expression of SOCS3 and IL-1Ra was monitored in motor cortex (6A-6C) and striatum (6D-6F) extracts by Western blot. Actin was run as loading control. Bands were scanned and values (SOCS3/Actin, 6B & 6E; IL-1Ra/Actin, 6C & 6F) are presented as relative to WT control for cortex (6B & 6C) and striatum (6E & 6F). Results are mean±SEM of four mice per group.

FIGS. 8A-8E. Gem treatment upregulates IL-1Ra in vivo in the striatum of $Cln2^{(-/-)}$ mice: $Cln2^{(-/-)}$ animals (4 weeks old) were treated with gem (dissolved in 0.1% MeC) orally at a dose of 7.5 mg/kg body weight/day. After 8 weeks of treatment, striatal sections were double-labeled for GFAP & IL-1Ra (8A) and Iba1 & IL-1Ra (8B). Total IL-1Ra$^+$ (8C), GFAP$^+$IL-1Ra$^+$ (8D) and Iba1$^+$IL-1Ra$^+$ (8E) cells were counted in two different sections of six different mice per group in an Olympus IX81 fluorescence microscope using the MicroSuite imaging software. Results are mean±SEM of six mice per group.

DETAILED DESCRIPTION

Figure 1A:
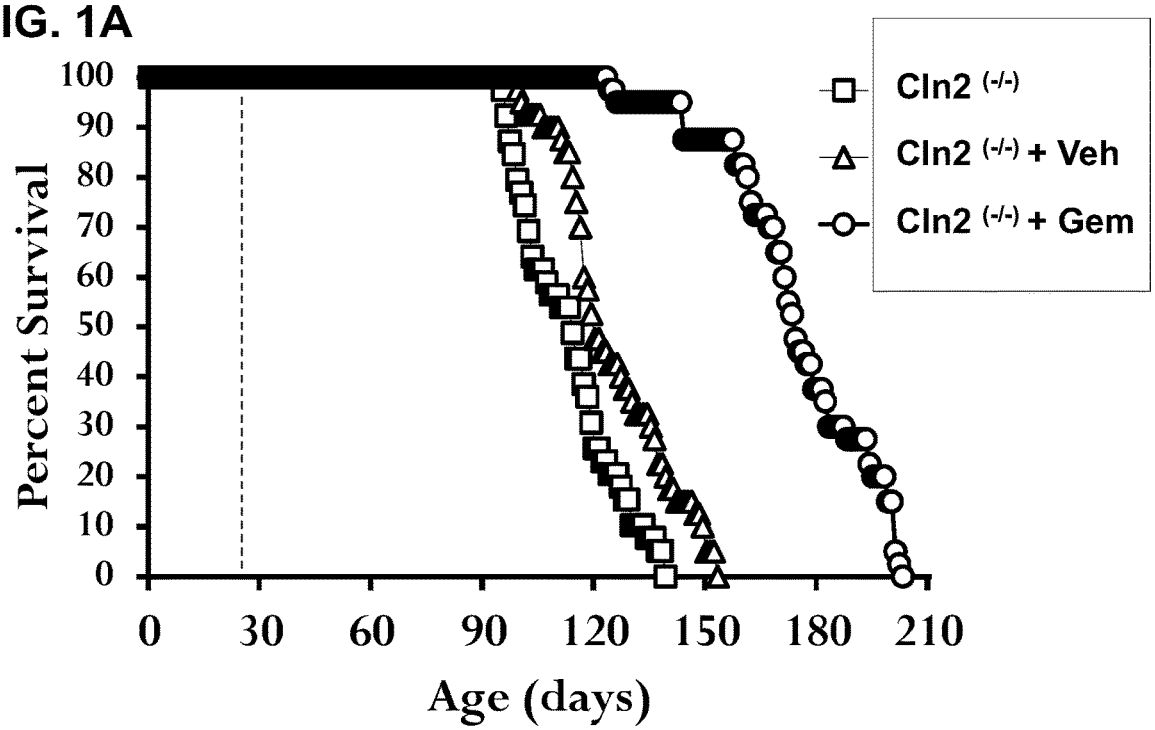
FIG. 1A-1B. Gemfibrozil (gem) prolongs the life span of $Cln2^{(-/-)}$ mice. $Cln2^{(-/-)}$ animals were treated with gem (dissolved in 0.1% MeC) orally at a dose of 7.5 mg/kg body weight/day. Treatment started from 4 weeks of age for all groups. One group of animals received only MeC as vehicle. 1A) Percentage of survival is shown by KaplanMeier plot. 1B) Mean survival days are shown for all three groups. Forty mice (n=40) containing 20 males and 20 female were used in each group.

The embodiments disclosed below are not intended to be exhaustive or to limit the scope of the disclosure to the precise form in the following description. Rather, the embodiments are chosen and described as examples so that others skilled in the art may utilize its teachings.

The present disclosure relates to methods of treatment of neurodegenerative disorders, including neuronal ceroid lipofuscinosis (NCL) and in particular late infantile neuronal ceroid lipofuscinosis (LINCL).

The agent may be a lipid-lowering drug such as a fibrate. Non-limiting examples of fibrates include gemfibrozil, fenofibrate, clofibrate, bezafibrate, ciprofibrate and clinofibrate.

Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the"

include plural references unless the context clearly dictates otherwise. The present disclosure also contemplates other embodiments "comprising," "consisting of" and "consisting essentially of," the embodiments or elements presented herein, whether explicitly set forth or not.

"Treating", "treat", or "treatment" as used herein, means an alleviation of symptoms associated with a disorder or disease, or halt of further progression or worsening of those symptoms, or prevention or prophylaxis of the disease or disorder. For example, within the context of this disclosure, successful treatment may include prevention of a neurodegenerative disease, an alleviation of symptoms related to neurodegenerative disease or a halting in the progression of a disease such as a neurodegenerative disease. As used herein, a control for measuring the treatment relative it a control is a subject that has not received the therapeutic agent.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

Methods of Treating a Neurodegenerative Disease

Provided herein are methods of treating a neurodegenerative disease. The neurodegenerative disease may be neuronal ceroid lipofuscinosis, Alzheimer's disease, Huntington's disease, Amyotrophic lateral sclerosis (ALS), Parkinson's disease, including Parkinson's plus diseases such as multiple system atrophy (MSA), progressive supranuclear palsy (PSP), corticobasal degeneration (CBD) or dementia with Lewy bodies (DLB). Batten disease is the most common form of a group of disorders called the neuronal ceroid lipofuscinosis (NCL). The neuronal ceroid lipofuscinosis (NCL) may be infantile NCL (INCL), Late Infantile Neuronal Ceroid Lipofuscinosis (LINCL), juvenile NCL (INCL), or adult NCL (ANCL). The neurodegenerative disease may be caused by a lysosomal storage disorder. The lysosomal storage disorder may be, for example, Tay-Sach's disease, Fabry disease, Niemann-Pick disease, Gaucher disease, Hunter Syndrome, Alpha-mannosidosis, Aspartylglucosaminuria, Cholesteryl ester storage disease, Chronic Hexosaminidase A Deficiency, Cystinosis, Danon disease, Farber disease, Fucosidosis, or Galactosialidosis.

NCL is a group of neurodegenerative diseases comprising typical autosomal recessive lysosomal storage disorders. NCLs may include clinical manifestations such as progressive mental deterioration, cognitive impairment, visual failure, seizures, and deteriorating motor function. NCLs may be associated with accumulation of autofluoroscent storage materials in neurons and/or other types of cells. NCLs may be divided into several types including Types 1 to 10, and the types may be based on the age of onset, ultra structural variations in accumulated storage materials, and genetic alterations. Presently, only one treatment is available for treatment of NCLs, especially LINCL. Rather, present treatment is merely supportive of disease symptoms.

Many types of NCL may be associated with mutations in the Cln genes. These mutations may be associated with a deficiency or loss of function. For example, late infantile neuronal ceroid lipofuscinosis (LINCL) may be associated with mutations in the gene Cln2, while infantile NCL (INCL) and juvenile (INCL) may be associated with mutations in the genes Cln1 and Cln3, respectively.

Agent

The agent may be a lipid-lowering drug such as a fibrate. Non-limiting examples of fibrates include gemfibrozil, fenofibrate, clofibrate, bezafibrate, ciprofibrate and clinofibrate. Gemfibrozil (5-(2,5-dimethylphenoxy)-2,2-dimethylpentanoic acid) is commercially available under the trademark Lopid® by Pfizer. Fenofibrate (2-(4-(4-chlorobenzoyl)phenoxy)-2-methyl-propanoic acid 1-methyl ethyl ester) is available commercially as Tricor® by Abbvie. Additional fibrates include Clofibrate (2-(4-chlorophenoxy)-2-methyl-propanoic ethyl ester), Bezafibrate (2-(4-(2-(4-chloro-benzoylamino)-ethyl)phenoxy)-2-methyl-propanoic acid), Ciprofibrate (2-(4-(2,2-dichlorocyclopropyl)phenoxy)-2-methyl propanoic acid) and Clinobibrate (2-[4-[1-[4-(2-carboxybutan-2-yloxy)phenyl]cyclohexyl]phenoxy]-2-methylbutanoic acid).

Pharmaceutical Compositions

The agent may be incorporated into pharmaceutical compositions suitable for administration to a subject (such as a patient, which may be a human or non-human).

The pharmaceutical compositions may include a "therapeutically effective amount" or a "prophylactically effective amount" of the agent. A "therapeutically effective amount" refers to an amount effective, at dosages and for periods of time necessary, to achieve the desired therapeutic result. A therapeutically effective amount of the composition may be determined by a person skilled in the art and may vary according to factors such as the disease state, age, sex, and weight of the individual, and the ability of the composition to elicit a desired response in the individual. A therapeutically effective amount is also one in which any toxic or detrimental effects of the agent are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

For example, a therapeutically effective amount of gemfibrozil may be about 5 mg to about 2000 mg, about 10 mg to about 1900 mg, about 15 mg to about 1800 mg, about 20 mg to about 1700 mg, about 25 mg to about 1600 mg, about 30 mg to about 1500 mg, about 35 mg to about 1400 mg, about 40 mg to about 1300 mg, about 45 mg to about 1200 mg, about 50 mg to about 1100 mg, about 55 mg to about 1000 mg, about 60 mg to about 900 mg, about 65 mg to about 800 mg, about 70 mg to about 700 mg, about 75 mg to about 600 mg, about 80 mg to about 500 mg, about 85 mg to about 400 mg, about 90 mg to about 300 mg, about 95 mg to about 200 mg, or about 100 mg to about 175 mg. In another example, the therapeutically effective amount of gemfibrozil may be about 600 mg or about 1200 mg.

For example, a therapeutically effective amount of fenofibrate may be about 5 mg to about 2000 mg, about 10 mg to about 1900 mg, about 15 mg to about 1800 mg, about 20 mg to about 1700 mg, about 25 mg to about 1600 mg, about 30 mg to about 1500 mg, about 35 mg to about 1400 mg, about 40 mg to about 1300 mg, about 45 mg to about 1200 mg, about 50 mg to about 1100 mg, about 55 mg to about 1000 mg, about 60 mg to about 900 mg, about 65 mg to about 800 mg, about 70 mg to about 700 mg, about 75 mg to about 600 mg, about 80 mg to about 500 mg, about 85 mg to about 400 mg, about 90 mg to about 300 mg, about 95 mg to about 200 mg, or about 100 mg to about 175 mg. In another example, the therapeutically effective amount of fenofibrate may be about 40 mg, about 48 mg, about 54 mg, about 67 mg, about 100 mg, about 120 mg, about 134 mg, about 145 mg, about 160 mg, or about 200 mg.

For example, a therapeutically effective amount of clofibrate may be about 5 mg to about 2000 mg, about 10 mg to about 1900 mg, about 15 mg to about 1800 mg, about 20 mg to about 1700 mg, about 25 mg to about 1600 mg, about 30 mg to about 1500 mg, about 35 mg to about 1400 mg, about 40 mg to about 1300 mg, about 45 mg to about 1200 mg, about 50 mg to about 1100 mg, about 55 mg to about 1000 mg, about 60 mg to about 900 mg, about 65 mg to about 800 mg, about 70 mg to about 700 mg, about 75 mg to about 600 mg, about 80 mg to about 500 mg, about 85 mg to about 400 mg, about 90 mg to about 300 mg, about 95 mg to about 200 mg, or about 100 mg to about 175 mg. In another example, the therapeutically effective amount of clofibrate may be about 500 mg.

The pharmaceutical compositions may include pharmaceutically acceptable carriers. The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Modes of Administration

Methods of treating neurological diseases such as late infantile neuronal ceroid lipofuscinosis may include any number of modes of administering the agent or pharmaceutical compositions of the agent. Modes of administration may include tablets, pills, dragees, hard and soft gel capsules, granules, pellets, aqueous, lipid, oily or other solutions, emulsions such as oil-in-water emulsions, liposomes, aqueous or oily suspensions, syrups, elixiers, solid emulsions, solid dispersions or dispersible powders. For the preparation of pharmaceutical compositions for oral administration, the agent may be admixed with commonly known and used adjuvants and excipients such as for example, gum arabic, talcum, starch, sugars (such as, e.g., mannitose, methyl cellulose, lactose), gelatin, surface-active agents, magnesium stearate, aqueous or non-aqueous solvents, paraffin derivatives, cross-linking agents, dispersants, emulsifiers, lubricants, conserving agents, flavoring agents (e.g., ethereal oils), solubility enhancers (e.g., benzyl benzoate or benzyl alcohol) or bioavailability enhancers (e.g. Gelucire™). In the pharmaceutical composition, the agent may also be dispersed in a microparticle, e.g. a nanoparticulate, composition.

For parenteral administration, the agent or pharmaceutical compositions of the agent can be dissolved or suspended in a physiologically acceptable diluent, such as, e.g., water, buffer, oils with or without solubilizers, surface-active agents, dispersants or emulsifiers. As oils for example and without limitation, olive oil, peanut oil, cottonseed oil, soybean oil, castor oil and sesame oil may be used. More generally spoken, for parenteral administration the agent or pharmaceutical compositions of the agent can be in the form of an aqueous, lipid, oily or other kind of solution or suspension or even administered in the form of liposomes or nano-suspensions.

The term "oral," as used herein, refers to modes of administration which include oral, enteral, buccal, sublabial, sublingual gastric and rectal administration.

The term "parenterally," as used herein, refers to modes of administration which include intravenous, intramuscular, intraperitoneal, intrasternal, subcutaneous and intraarticular injection and infusion.

The present disclosure has multiple aspects, illustrated by the following non-limiting examples.

EXAMPLES

Example 1: Materials and Methods

Reagents and Antibodies:

Reagents for TUNEL assay on frozen brain sections were purchased from EMD Millipore (Billerica, Mass.) and experiments were performed according to manufacturer's protocol. Blocking buffer and secondary antibodies for immune blot (IB) (IRDye 700 or IRDye 800—labelled) were purchased from Licor (Lincoln, Nebr.). Secondary antibodies for immunohistochemistry (IHC) (FITC or Cy5—labeled) were purchased from Jackson ImmunoResearch (West Grove, Pa.). Sources of primary antibodies used in this study along with their applications and dilutions are listed in Table 1.

Animals:

Animal maintaining and experiments were in accordance with National Institute of Health guidelines and were approved by the Institutional Animal Care and Use committee (IACUC) of the Rush University of Medical Center, Chicago, Ill. Animals exhibiting mild seizures and tremors were fed and watered through animal feeding needles. However, if any mouse came to the moribund stage, it was decapitated after anesthesia with ketamine/xylazine injectables. Conditions for moribund were as follows: central nervous system disturbance (head tilt, seizures, tremors, circling, spasticity, and paresis); inability to remain upright; evidence of muscle atrophy; chronic diarrhea or constipation; rough coat and distended abdomen; preading area of alopecia caused by disease; coughing, rales, wheezing and nasal discharge; distinct jaundice and/or paleness (anemia); markedly discolored urine, polyuria or anuria; frank bleeding from any orifice; persistent self-induced trauma. $Cln2^{(+/-)}$ animals were kindly provided by Dr. Peter Lobel (Center for Advanced Biotechnology and Medicine, Robert Wood Johnson Medical School, Piscataway, N.J., USA). These animals were inbred and subsequent generations were screened by RTPCR to further obtain $Cln2^{(+/+)}$, $Cln2^{(+/-)}$ and $Cln2^{(-/-)}$ strains. These $Cln2^{(-/-)}$ animals have undetectable TPP1 activity and mimic similar features of human disease including diminished motor behavior, reduced longevity, increased neuropathology in the CNS, and enhanced glial activation (Sleat et al. 2004).

Treatment of $Cln2^{(-/-)}$ Mice with Gemfibrozil (Gem):

Age- and sex-matched $Cln2^{(+/+)}$ mice from the same background were used as wild type (WT) controls and Cln2$^{(-/-)}$ animals were used in different treatment groups. Gem (7.5 mg/kg body wt/day) was dissolved in DMSO followed by dilution in 0.1% methyl cellulose (MeC). Cln2$^{(-/-)}$ mice were either not fed (Un-untreated group), gavaged with 0.1% MeC (vehicle treated group) or gavaged with gem (gem-treated group) for 8 weeks for biochemical studies. Similar treatment regimen was followed as long as the animals are not considered to be morbid as described above for survival study. Here, 40 mice (20 male and 20 female) were used per group and animals (4 weeks old) were randomly selected for any group.

Locomotor Activity:

Locomotor activities were measured in Cln2$^{(-/-)}$ mice after 8 weeks of gem treatment using Digiscan Monitor (Omnitech Electronics, Inc., Columbus, Ohio) as described by us (Khasnavis & Pahan 2014, Ghosh et al. 2007, Ghosh et al. 2009). This Digiscan Monitor records basic locomotion parameters, such as horizontal activity, total distance traveled, movement time, rest time, etc. as well as stereotypy, behavior that is directly controlled by striatum. Briefly, mice were removed directly from their cages and gently placed nose first into a specified corner of the open-field apparatus and after release, data acquisition began every five min interval. DIGISCAN software was used to analyze and store horizontal and vertical activity data, which were monitored automatically by infra-red beams. Here, 12 animals were used per group. After open field tests, six of these mice (n=6) were perfused for immunohistochemical analysis and four mice (n=4) were used for Western blot analysis.

Immunohistochemistry and Cell Counting:

After 8 weeks of treatment, mice were sacrificed and their brains fixed, embedded, and processed. Sections (30 μm) were made from different brain regions (motor cortex and striatum) using a Leica Cryostat and immunofluorescence staining on fresh frozen sections was performed as described (Corbett et al. 2015, Roy et al. 2015, Roy et al. 2016). Briefly, before adding blocking buffer (2% BSA in PBS), sections were incubated in 100 mM glycine for 20 min for reducing autofluorescence. For details on antibody concentrations, please see Table 1. The samples were mounted and observed under Olympus IX41 fluorescence microscope. Counting analysis was performed using the Olympus Microsuite V software for imaging applications with the help of touch counting module (Corbett et al. 2015, Roy et al. 2015). After acquiring images under 20×objective lens, images were further analyzed as follows. Before counting cells, the entire image area was calibrated with the help of a rectangular box available in the touch counting panel. Once the area of the image was measured, touch counting program was applied to count number of fluorescent signals using simple mouse click method. Next, the total number of signals in a given area was divided by the total area of the image and presented as number of cells per square millimeter unit.

Detection of Storage Materials:

It was performed by monitoring subunit c of mitochondrial ATP synthase (SCMAS) by immunofluorescence. Please see Table 1 for details on antibody dilutions. DAPI was used to monitor nucleus. SCMAS-associated fluorescence intensity was quantified by using the Olympus Microsuite V software. Briefly, captured images were opened in the infinity image viewer and the contour was drawn around the granules to obtain the fluorescence intensity.

Immunoblot Analysis:

After 8 weeks of treatment, mice were sacrificed and cortex and striatum regions were isolated, homogenized in RIPA buffer (150 mM sodium chloride, 1.0% NP-40 or Triton X-100, 0.5% sodium deoxycholate, 0.1% SDS (sodium dodecyl sulphate), 50 mM Tris, pH 8.0), supernatant was taken and protein was estimated by BioRad protein assay. Equal amounts of protein from the tissue extract were separated in 12% or 15% Bis-Tris gels and proteins were transferred onto a nitrocellulose membrane (Bio-Rad) using the Thermo-Pierce Fast Semi-Dry Blotter (Corbett et al. 2015, Roy et al. 2015, Roy et al. 2016). The membrane was then washed for 15 min in TBS plus Tween 20 (TBST) and blocked for 1 h in TBST containing BSA. Next, membranes were incubated overnight at 4° C. under shaking conditions with the antibodies for the following proteins: β-Actin, IL-1Ra, phospho-Bad, and SOCS3. Please see Table 1 for details on antibody dilutions. The next day, membranes were washed in TBST for 1 h, incubated in secondary antibodies against primary antibody hosts (all 1:10,000; Jackson ImmunoResearch) for 1 h, washed for one more h and visualized under the Odyssey® Infrared Imaging System (Li-COR, Lincoln, Nebr.).

Statistical Analysis:

All values are expressed as means±SEM. One-way ANOVA followed by Tukey's or Scheffé's post hoc tests, Student's t tests and KaplanMeier survival estimators ($\chi^2$) were used for data analyses, using SPSS 19.

Example 2: Gem Treatment Prolongs the Lifespan in Cln2$^{(-/-)}$ Mice

Figure 1B:
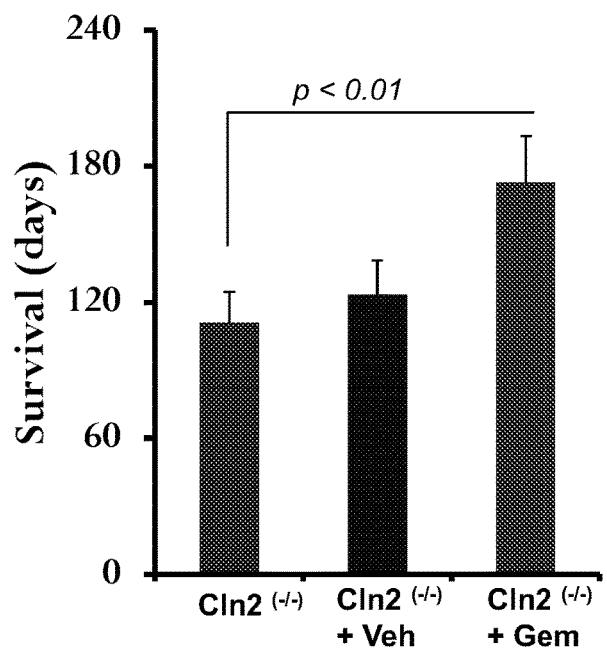

Cln2$^{(-/-)}$ mouse serves as an important animal model for testing new therapeutic approaches against LINCL (Cabrera-Salazar et al. 2007, Sleat et al. 2008, Chang et al. 2008, Sleat et al. 2004). Usually, LINCL progresses rapidly, ending in death between ages 8 and 10 (Sohar et al. 1999, Sleat et al. 1997). Similarly, Cln2$^{(-/-)}$ mice also die within 140 d (Sleat et al. 2004). Therefore, at first, we examined whether oral gem treatment was capable of increasing the lifespan of Cln2$^{(-/-)}$ mice. Earlier we have demonstrated that after oral administration, gem enters into the CNS (Dasgupta et al. 2007). Mice were treated daily with gem (7.5 mg/kg body weight/day) via gavage from 4 weeks of age. Since gem was solubilized in 0.1% methyl cellulose, one group of Cln2$^{(-/-)}$ mice also received 0.1% methyl cellulose as vehicle. Untreated Cln2$^{(-/-)}$ male and female mice started dying from 95 days and within 137 days, all Cln2$^{(-/-)}$ mice died (FIG. 1A). In terms of survival, we did not see any difference between male and female Cln2$^{(-/-)}$ mice. However, gem-treated Cln2$^{(-/-)}$ mice survived until 204 days, suggesting that gem is capable of increasing the lifespan of Cln2$^{(-/-)}$ mice by more than 2 months (FIG. 1A). On the other hand, all vehicle-treated mice died within 150 days (FIG. 1A), suggesting very mild protection by vehicle only. These results are also supported by mean survival days of each group of mice (FIG. 1B).

Example 3: Gem Treatment Improves Motor Behavior in Cln2$^{(-/-)}$ Mice

Together with increase in longevity, another therapeutic goal of neuroprotection for LINCL patients is to decrease functional impairment. Therefore, to examine whether gem increases not only longevity but also improves motor behavior in Cln2$^{(-/-)}$ mice, we monitored locomotor activities. Locomotor activities were monitored 8 weeks after gem treatment. Cln2$^{(-/-)}$ mice exhibited marked decrease in horizontal activity (FIG. 2A), movement time (FIG. 2B), number of movement (FIG. 2C), total distance traveled (FIG. 2D), and stereotypy counts (FIG. 2E) as compared to WT mice. On the other hand, the rest time was more in Cln2$^{(-/-)}$ mice than WT mice (FIG. 2F). However, oral administration of gem significantly improved locomotor activities in Cln2$^{(-/-)}$ mice (FIG. 2A-F).

Figure 3A:
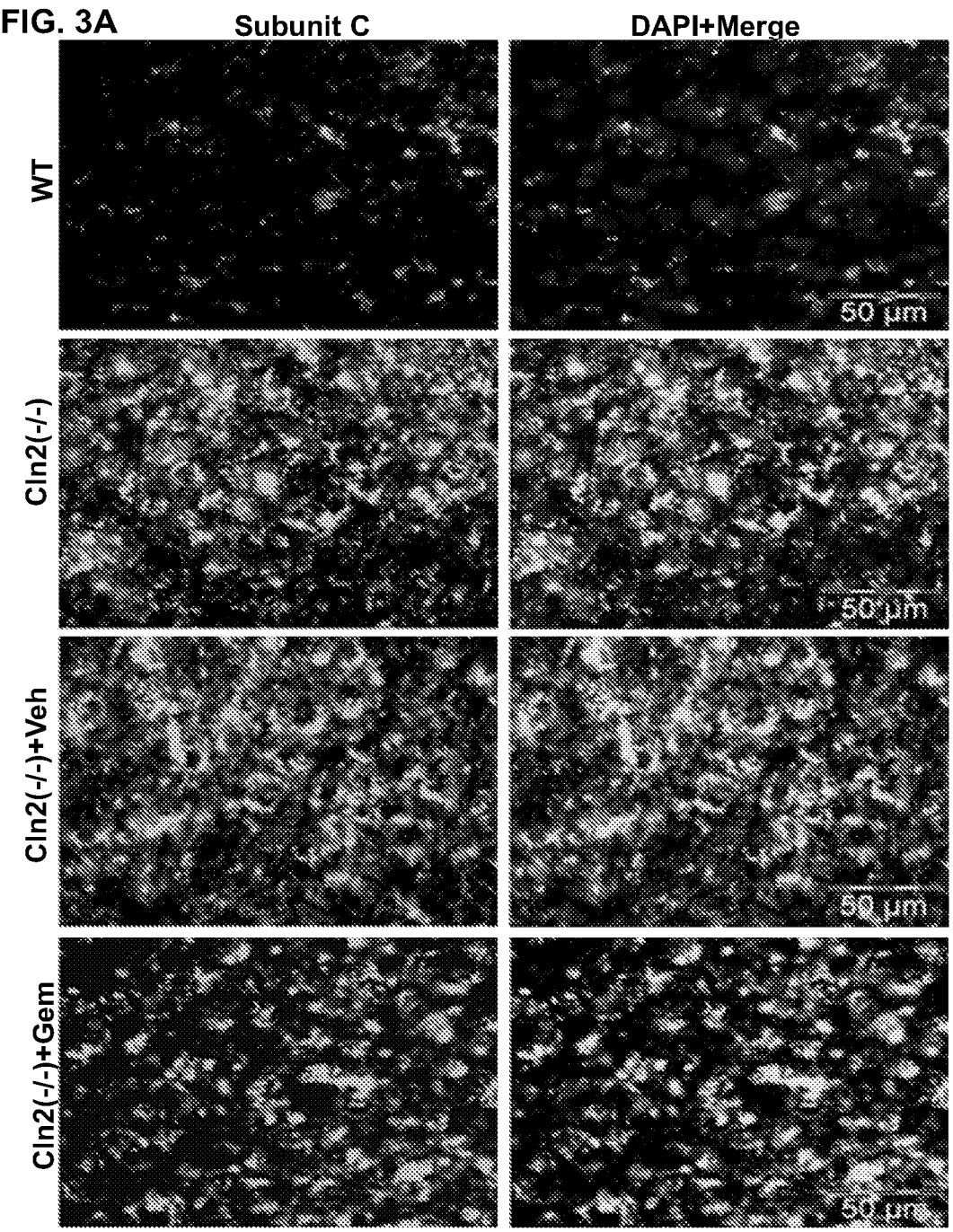
FIG. 3A-3B. Gem treatment reduces storage materials in vivo in the motor cortex of $Cln2^{(-/-)}$ mice: $Cln2^{(-/-)}$ animals (4 weeks old) were treated with gem (dissolved in 0.1% MeC) orally at a dose of 7.5 mg/kg body weight/day. After 8 weeks of treatment, storage pigments were observed in cortical sections by immunofluorescence analysis of subunit C (3A). DAPI was used to visualize nucleus. 3B) Subunit C positive immunofluorescence was quantified in two different sections (two images per section) of each of six different mice (n=6) per group using NIH Image J software as described under Methods section. $^{a}p<0.001$ vs WT-control; $^{b}p<0.05$ vs $Cln2^{(-/-)}$.
Figure 3B:
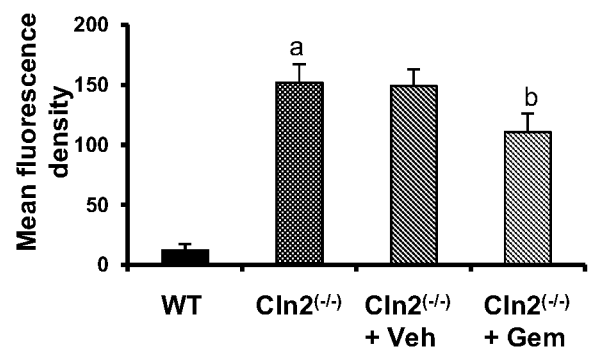

Example 4: Gem Treatment Lowers the Burden of Storage Material in the Brain of Cln2$^{(-/-)}$ Mice One of the common characteristics of lysosomal storage disorders including LINCL is the accumulation of autofluorescent inclusion bodies in all tissues including the brain (Boustany 2013, Hachiya et al. 2006). Recently we delineated that gemfibrozil is capable of stimulating lysosomal biogenesis via PPARα-mediated transcriptional upregulation of TFEB (Ghosh et al. 2015). Since gem treatment prolongs the lifespan and improves the motor behavior of Cln2$^{(-/-)}$ mice, we examined whether gem treatment could reduce the load of storage material in vivo in the motor cortex. As expected, we observed marked increase in subunit c of mitochondrial ATP synthase (SCMAS) accumulation in the motor cortex of Cln2$^{(-/-)}$ mice as compared to WT mice (FIG. 3A-B). However, gem treatment of Cln2$^{(-/-)}$ mice led to significant decrease in SCMAS (FIG. 3A-B). These results were specific as vehicle treatment did not result in such decrease in storage materials (FIG. 3A-B).

Example 5: Gem Treatment Prevents Neuronal Apoptosis in the Brain of Cln2(-/-) Mice As seen in other neurodegenerative disorders (Cotman & Anderson 1995, Saha & Pahan 2006), apoptosis is also responsible for neuronal degeneration in LINCL (Dhar et al. 2002, Puranam et al. 1997, Lane et al. 1996). Therefore, we examined whether gem treatment was capable of suppressing neuronal apoptosis in the CNS of Cln2$^{(-/-)}$ mice. It is evident from FIG. 4A-B that NeuN-positive neurons underwent apoptosis in the motor cortex of Cln2$^{(-/-)}$ mice.

Figure 5A:
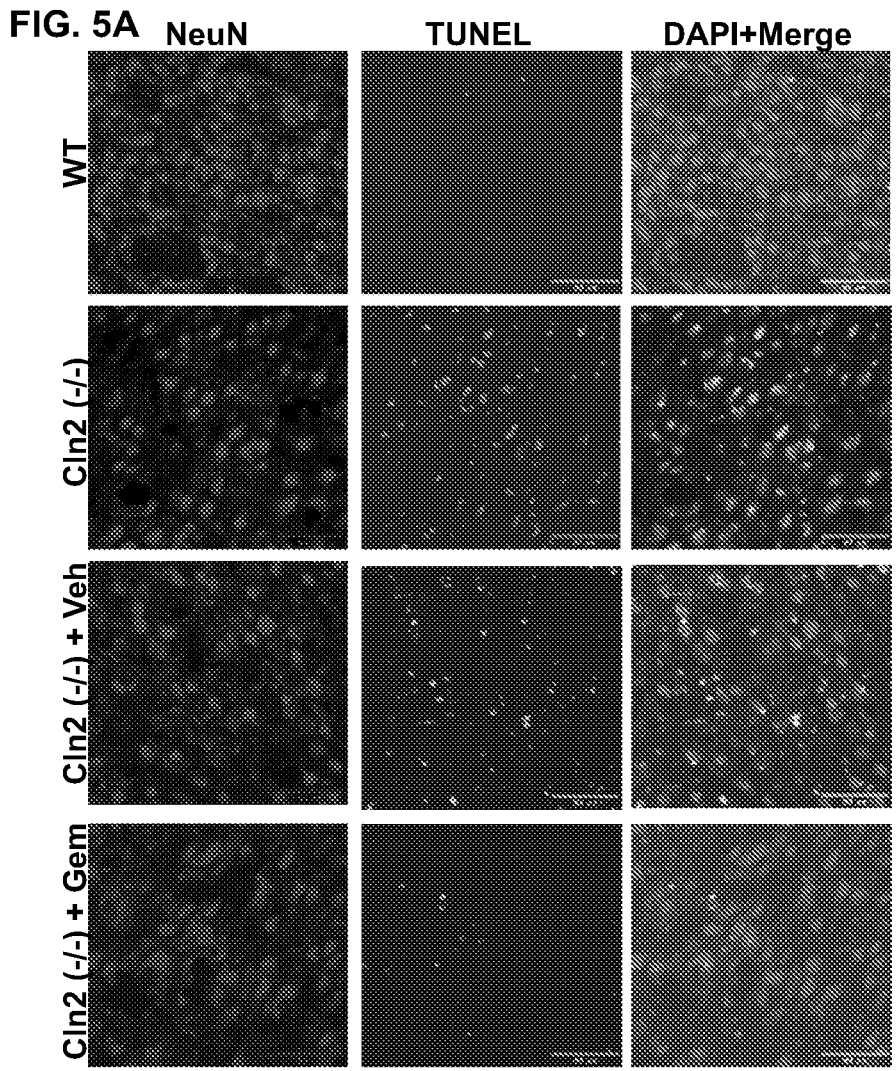
FIGS. 5A-5D. Gem treatment inhibits apoptosis in vivo in the striatum of $Cln2^{(-/-)}$ mice: $Cln2^{(-/-)}$ animals (4 weeks old) were treated with gem (dissolved in 0.1% MeC) orally at a dose of 7.5 mg/kg body weight/day. After 8 weeks of treatment, striatal sections were double-labeled for NeuN and TUNEL (5A). NeuN$^+$TUNEL$^+$ cells were counted (5B) in two different sections of each of six different mice (n=6) per group in an Olympus IX81 fluorescence microscope using the MicroSuite imaging software. 5C) Striatal homogenates were immunoblotted for phospho-BAD. Actin was run as loading control. 5D) Bands were scanned and values (P-BAD/Actin) are presented as relative to WT control. Results are mean±SEM of four mice per group.
Figure 5B:
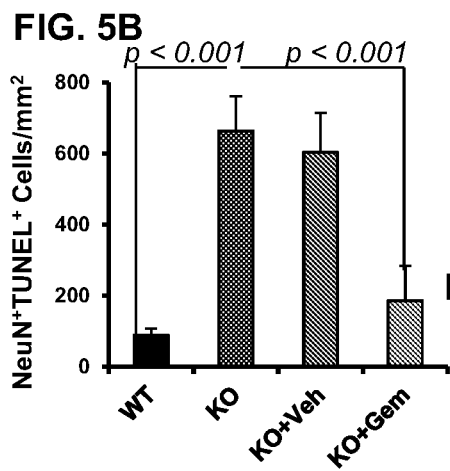
Figure 5C:
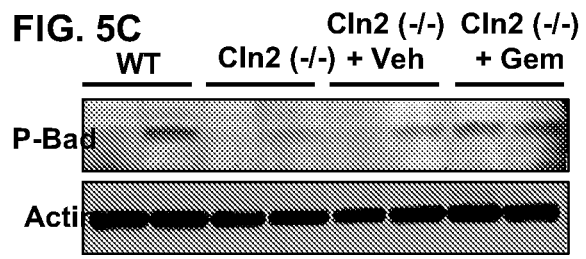
Figure 5D:
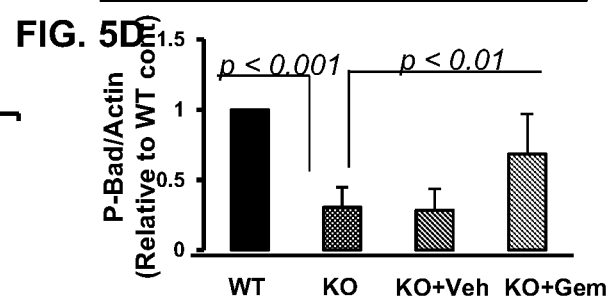

However, oral treatment of gem strongly inhibited neuronal apoptosis in vivo in the motor cortex (FIG. 4A-B). These results are specific as vehicle (0.1% methyl cellulose) treatment did not suppress neuronal apoptosis (FIG. 4A-B). Although BAD is an apoptotic molecule, phosphorylation of BAD is known to support cell survival (Datta et al. 1999, Datta et al. 2002). Therefore, we examined the level of phospho-BAD (P-BAD) in the motor cortex of Cln2$^{(-/-)}$ mice. Consistent to increased apoptosis, the level of P-BAD decreased in the motor cortex of Cln2$^{(-/-)}$ mice (FIGS. 4C-D). However, treatment of Cln2$^{(-/-)}$ mice with gem, but not vehicle, led to upregulation of P-BAD (FIGS. 4C-D). To understand whether the effect of gem is confined to motor cortex or other part of the brain is also benefited by gem treatment, we monitored apoptosis in striatum. Similar to motor cortex, we also observed increase in apoptosis (FIGS. 5A-B) and decrease in P-BAD (FIG. 5C-D) in the striatum of Cln2$^{(-/-)}$ mice. However, gem treatment reduced neuronal apoptosis (FIGS. 5A-B) and increased the level of P-BAD (FIGS. 5C-D) in vivo in the striatum, suggesting that oral gem treatment is capable of suppressing apoptosis in different parts of the brain of Cln2$^{(-/-)}$ mice.

Figure 7A:
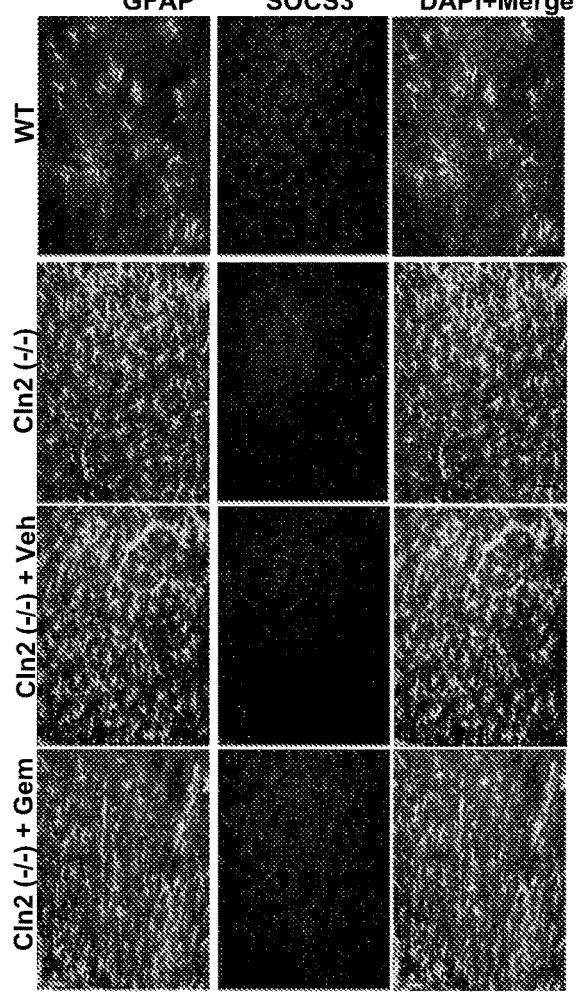
FIGS. 7A-7E. Gem treatment upregulates SOCS3 in vivo in the striatum of $Cln2^{(-/-)}$ mice: $Cln2^{(-/-)}$ animals (4 weeks old) were treated with gem (dissolved in 0.1% MeC) orally at a dose of 7.5 mg/kg body weight/day. After 8 weeks of treatment, striatal sections were double-labeled for GFAP & SOCS3 (7A) and Iba1 & SOCS3 (7B). Total SOCS3+ (7C), GFAP$^+$SOCS3$^+$ (7D) and Iba1$^+$SOCS3$^+$ (7E) cells were counted in two different sections of six different mice per group in an Olympus IX81 fluorescence microscope using the MicroSuite imaging software. Results are mean±SEM of six mice per group.
Figure 7B:
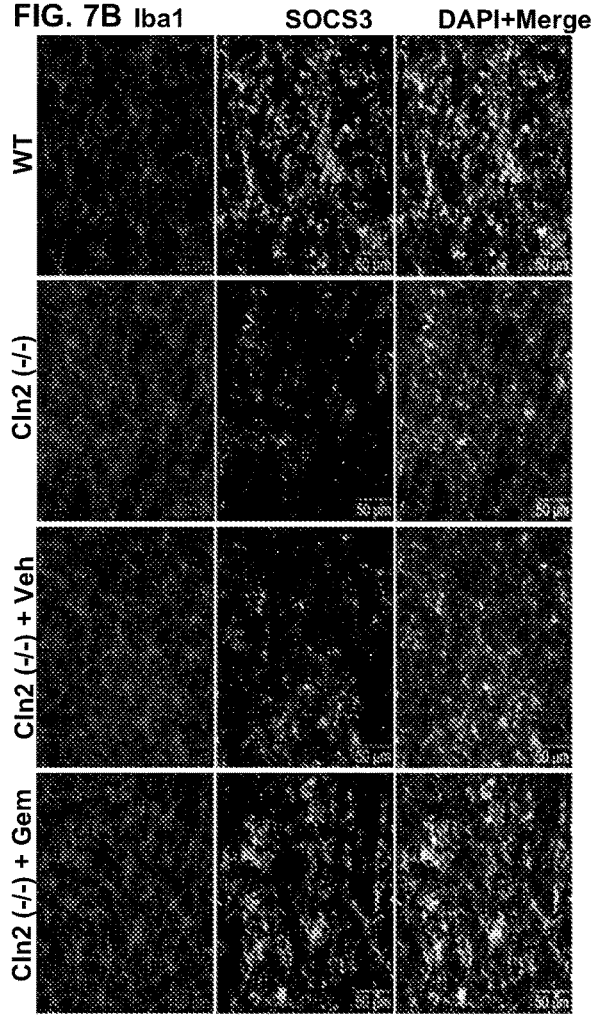
Figure 7C:
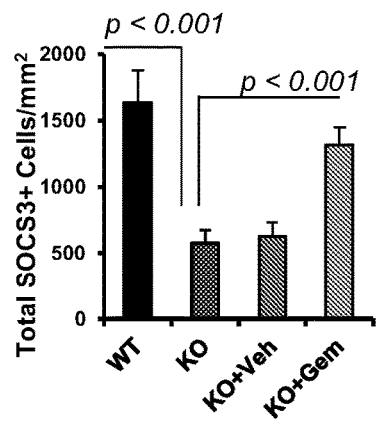
Figure 7D:
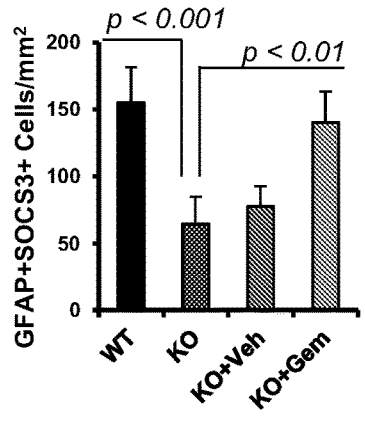
Figure 7E:
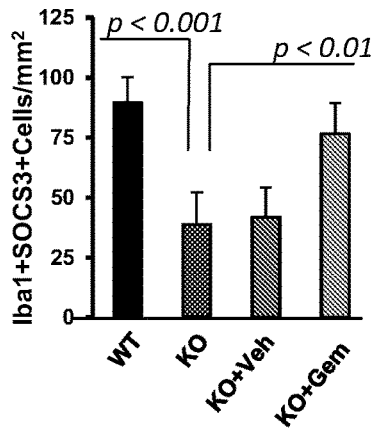

Example 6: Gem Increases the Levels of Anti-Inflammatory Factors in the Brain of Cln2$^{(-/-)}$ Mice We have demonstrated that gem is anti-inflammatory (Jana & Pahan 2012, Jana et al. 2007, Pahan et al. 2002) and that gem increases the level of SOCS3 and IL-1Ra, anti-inflammatory factors, in different brain cells (Corbett et al. 2012, Ghosh & Pahan 2012b). Therefore, here, we investigated whether gem treatment could upregulate these anti-inflammatory molecules in vivo in the brain of Cln2$^{(-/-)}$ mice. At 12 weeks of age, we observed decrease in SOCS3 and IL-1Ra in motor cortex (FIGS. 6A-C) and striatum (FIGS. 6D-F) of Cln2$^{(-/-)}$ mice as compared to age-matched WT mice. However, after 8 weeks of oral treatment with gem, but not vehicle, the increase in SOCS3 (FIGS. 6A, B, D, & E) and IL-1Ra (FIGS. 6A, D, C, & F) was seen in both motor cortex and striatum of Cln2$^{(-/-)}$ mice. To confirm these findings further, next, we performed double-label immunofluorescence in striatal sections. Although we observed more astroglia (FIG. 7A) and microglia (FIG. 7B) in striatal sections of Cln2$^{(-/-)}$ mice as compared to WT mice, there was a loss of SOCS3 in the former as compared to the latter (FIGS. 7A-C). However, similar to Western blot results, marked increase in SOCS3 was seen in the striatum of Cln2$^{(-/-)}$ mice after gem treatment (FIGS. 7A-C). This increase in SOCS3 was visible inastrocytes (FIGS. 7A & D), microglia (FIGS. 7B & E) as well as other brain cells (FIG. 7). Similar to SOCS3, we also noticed the loss of IL-1Ra in the striatum of Cln2$^{(-/-)}$ mice as compared to WT mice (FIGS. 8A-E). However, treatment of Cln2$^{(-/-)}$ mice with gem, but not vehicle, led to restoration and/or upregulation of IL-1Ra in the striatum (FIGS. 8A-E). Again, gem-induced increase in IL-1Ra in vivo in the striatum of Cln2$^{(-/-)}$ mice was in both astrocytes (FIGS. 8A & D) and microglia (FIGS. 8B & E). Interestingly, in both motor cortex and striatum of Cln2$^{(-/-)}$ mice, we did not observe any reduction in either astroglia or microglia after gem treatment (FIGS. 7 & 8), suggesting that once astrogliosis or microgliosis occurs in vivo in the brain of a chronic neurodegenerating condition as found in Cln2$^{(-/-)}$ mice, gemfibrozil treatment may only modulate their function towards the anti-inflammatory mode without decreasing its number.

Discussion of Examples 2-6

Mutations in the Cln2 result in deficiency and/or loss of function of the TPP1 enzyme, ultimately causing LINCL (Bellettato & Scarpa 2010, Walus et al. 2010, Sohar et al. 1999). Although enzyme replacement therapy and gene therapy clinical trials are ongoing, no established drug mediated therapy is currently available for LINCL. Therefore, development of neuroprotective therapeutic approaches for delaying the disease progression, improving locomotor functions and increasing the survival of LINCL patients are of paramount importance. Cln2$^{(-/-)}$ mouse is useful in determining new therapeutic strategies and testing the efficacy of new drugs for LINCL. Here, we demonstrate for the first time that gemfibrozil (gem), an FDA-approved drug for hyperlipidemia in humans, improves locomotor functions and prolongs the lifespan in Cln2$^{(-/-)}$ mice. Recently we have delineated that gemfibrozil is capable of upregulating TPP1 in cultured mouse and human brain cells and in vivo in mouse brain via PPARα/RXRα pathway (Ghosh et al. 2012). However, there is no TPP1 in Cln2$^{(-/-)}$ mice. Therefore, in this case, gem is employing TPP1-independent mechanisms to delay the disease progression in Cln2$^{(-/-)}$ mice.

Although the importance of autofluorescent storage materials in the pathogenesis of LSDs including LINCL is not known, these inclusion bodies are one of hallmarks of LSDs (Boustany 2013). Recently we have also demonstrated that gem is capable of stimulating lysosomal biogenesis via PPARα-mediated transcriptional activation of TFEB (Ghosh et al. 2015), suggesting possible lowering of storage materials by gem treatment. Accordingly, gem was able to reduce storage materials from the motor cortex of Cln2$^{(-/-)}$ mice. Therefore, even in the absence of TPP1 (a vital enzyme in the degradation pathway), gem can stimulate autophagic clearance via TFEB-mediated activation of other lysosomal enzymes. Earlier we have demonstrated that in skin fibroblasts of patients with LINCL, a combination of gemfibrozil and retinoic acid increased lysosomal biogenesis irrespective of the disease status (Ghosh et al. 2015).

Neuronal apoptosis is a hallmark of most of the known neurodegenerative diseases including lysosomal storage disorders (Dhar et al. 2002, Puranam et al. 1997, Lane et al. 1996). Strong inhibition of neuronal apoptosis in different parts of the CNS of Cln2$^{(-/-)}$ mice by gem suggests that this anti-apoptotic property of gem may contribute to its lifespan-prolonging efficacy in these mice. BAD, a member of the BCL-2 family, is an important regulator of apoptosis (Datta et al. 1999, Datta et al. 2002). Non-phosphorylated form BAD is known to induce apoptosis by forming heterodimers with survival proteins Bcl-x and Bcl-2, thereby allowing two other pro-apoptotic proteins, BAK and BAX, to aggregate and induce release of cytochrome c (Datta et al. 1999, Datta et al. 2002). On the other hand, phosphorylated BAD is sequestered in the cytoplasm by binding to 14-3-3 and thereby allowing cell survival. Here, we have demonstrated that gem treatment restores/upregulates the level of P-BAD in motor cortex and striatum of Cln2$^{(-/-)}$ mice. Signaling mechanisms leading to phosphorylation of BAD is becoming clear. Phosphatidylinositol-3 kinase (PI3K) is a key signaling molecule implicated in the regulation of a broad array of biological responses including cell survival (Koyasu 2003). Several studies have shown that activation of PI3K leads to phosphorylation of BAD via Akt (Ellert-Miklaszewska et al. 2005, Li et al. 2001). Interestingly, gem induces the activation of p85α-associated type IA PI3K in brain cells (Jana et al. 2007). Therefore, it is possible that gem suppresses apoptosis in the CNS of Cln2$^{(-/-)}$ mice via PI3K-(P)BAD pathway.

Although there are many causes of apoptosis in the CNS, neuroinflammation is an important one. Therefore, chronic inflammation mediated by activated glial cells is becoming a hallmark of several neurodegenerative disorders including LINCL (Shyng & Sands 2014, Cooper et al. 2015, Macauley et al. 2014). IL-1β, a proinflammatory cytokine, is implicated in the pathogenesis of neurodegenerative diseases. Although IL-1β binds to its high-affinity receptor, IL-1R, and upregulates proinflammatory signaling pathways, IL-1R antagonist (IL-1Ra) adheres to the same receptor and inhibits proinflammatory cell signaling (Basu et al. 2004). Similarly, suppressor of cytokine signaling (SOCS) proteins also play a crucial role in inhibiting cytokine signaling and inflammatory gene expression in various cell types, including glial cells (Baker et al. 2009, Chen et al. 2000). Therefore, upregulation of IL-1Ra and SOCS is considered important in attenuating inflammation. Recently, we have seen that gem upregulates SOCS3 in glial cells via PI3K-mediated activation of KLF4 (Ghosh & Pahan 2012b) and that gem increases IL-1Ra via PI3K-mediated activation of CREB (Corbett et al. 2012). It is important to see that gem treatment increased the level of both SOCS3 and IL-1Ra in striatum and cortex of Cln2$^{(-/-)}$ mice. Therefore, by upregulating these important anti-inflammatory molecules, gem may exhibit protection and delay the disease onset in Cln2$^{(-/-)}$ mice.

Gem has several advantages over other prospective neuroprotective agents. For example, gem is an oral drug and fairly nontoxic (Backes et al. 2007, Roy & Pahan 2009, Pahan 2006). It has been well tolerated in human and animal studies. Known as 'Lopid' in the pharmacy, it is a commonly used lipid-lowering drug in humans since FDA approval in 1981. The Veterans Affairs High-Density Lipoprotein Intervention Trial (VA-HIT) has reported that coronary heart disease events are significantly reduced by gem in patients when the predominant lipid abnormality was low HDL-C (Robins et al. 2001). In a double-blind, randomized, placebo controlled trial, this drug was shown to reduce small low-density lipoprotein more in normolipemic subjects classified as low-density lipoprotein pattern B compared with pattern A (Superko et al. 2005). Another recent trial showed that low-density lipoprotein and HDL particle subclasses are favorably changed by gem therapy (Otvos et al. 2006). Gem also lowers triglycerides and raises HDL with reasonable safety in a pediatric population with metabolic syndrome (Smalley & Goldberg 2008).

In summary, we have demonstrated that gemfibrozil, an FDA-approved lipid-lowering drug in humans, reduces storage materials, upregulates anti-inflammatory molecules, suppresses neuronal apoptosis, and increases the lifespan of Cln2$^{(-/-)}$ mice. Although in vivo situation of Cln2$^{(-/-)}$ mouse brain and its treatment with gem may not truly resemble the in vivo neurodegenerative situation in patients with LINCL, our results identify gem as a possible therapeutic agent to prolong the lifespan in LINCL patients.

The above Figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims.

TABLE 1

Antibodies, sources, applications, and dilutions used

| Target | Antibody (Clone) | Epitope/Immunogen | Application/ Dilution | Source; Catalog |
|---|---|---|---|---|
| β-Actin | Mouse monoclonal (AC-15) | a.a. 1-15 of *Xenopus laevis* β-actin | WB - 1:5000 | Abcam; ab6276 |
| Subunit C of ATP synthase | Rabbit monoclonal | Synth peptide, a.a. 50-C terminus Human ATP synthase | IHC - 1:100 | Abcam; ab181243 |
| GFAP | Rabbit polyclonal | Synth peptide to cow GFAP | IHC - 1:2000 | Dako; z0334 |
| Iba1 | Goat polyclonal | Synth peptide a.a. 135-147 Human Iba1 (C terminus) | IHC - 1:500 | Abcam; ab5076 |
| NeuN | Mouse monoclonal (A60) | Purified mouse brain nuclei | IHC - 1:500 | Millipore; MAB377 |
| P-BAD | Rabbit polyclonal | P-BAD (Ser 136) | WB - 1:300 | Cell Signaling; # 9295 |
| SOCS3 | Rabbit polyclonal | C-terminus of human SOCS3 | WB - 1:500 IHC - 1:200 | Abcam; ab16030 |
| IL-1Ra | Rabbit monoclonal | Human IL-1RA aa 150 to the C-terminus | WB - 1:500 IHC - 1:200 | Abcam; ab124962 |

WB, Western blot; IHC, immunohistochemistry; GFAP, glial fibrillary acidic protein; SOCS3, suppressor of cytokine signaling 3; IL-1Ra, Interleukin-1 receptor antagonist

REFERENCES

Backes, J. M., Gibson, C. A., Ruisinger, J. F. and Moriarty, P. M. (2007) Fibrates: what have we learned in the past 40 years? *Pharmacotherapy*, 27, 412-424.

Baker, B. J., Akhtar, L. N. and Benveniste, E. N. (2009) SOCS1 and SOCS3 in the control of CNS immunity. *Trends Immunol*, 30, 392-400.

Basu, A., Krady, J. K. and Levison, S. W. (2004) Interleukin-1: a master regulator of neuroinflammation. *J Neurosci Res*, 78, 151-156.

Bellettato, C. M. and Scarpa, M. (2010) Pathophysiology of neuropathic lysosomal storage disorders. *J Inherit Metab Dis*, 33, 347-362.

Boustany, R. M. (2013) Lysosomal storage diseases—the horizon expands. *Nat Rev Neurol*, 9, 583-598.

Cabrera-Salazar, M. A., Roskelley, E. M., Bu, J. et al. (2007) Timing of therapeutic intervention determines functional and survival outcomes in a mouse model of late infantile batten disease. *Mol Ther*, 15, 1782-1788.

Chang, M., Cooper, J. D., Sleat, D. E., Cheng, S. H., Dodge, J. C., Passini, M. A., Lobel, P. and Davidson, B. L. (2008) Intraventricular enzyme replacement improves disease phenotypes in a mouse model of late infantile neuronal ceroid lipofuscinosis. *Mol Ther*, 16, 649-656.

Chen, X. P., Losman, J. A. and Rothman, P. (2000) SOCS proteins, regulators of intracellular signaling. *Immunity*, 13, 287-290.

Cooper, J. D., Tarczyluk, M. A. and Nelvagal, H. R. (2015) Towards a new understanding of NCL pathogenesis. *Biochim Biophys Acta*, 1852, 2256-2261.

Corbett, G. T., Gonzalez, F. J. and Pahan, K. (2015) Activation of peroxisome proliferator-activated receptor alpha stimulates ADAM10-mediated proteolysis of APP. *Proc Natl Acad Sci USA*, 112, 8445-8450.

Corbett, G. T., Roy, A. and Pahan, K. (2012) Gemfibrozil, a Lipid-Lowering Drug, Upregulates IL-1 Receptor Antagonist in Mouse Cortical Neurons: Implications for Neuronal Self-Defense. *J Immunol*, 189, 1002-1013.

Cotman, C. W. and Anderson, A. J. (1995) A potential role for apoptosis in neurodegeneration and Alzheimer's disease. *Mol Neurobiol*, 10, 19-45.

Dasgupta, S., Roy, A., Jana, M., Hartley, D. M. and Pahan, K. (2007) Gemfibrozil ameliorates relapsing-remitting experimental autoimmune encephalomyelitis independent of peroxisome proliferator-activated receptor-alpha. *Mol Pharmacol*, 72, 934-946.

Datta, S. R., Brunet, A. and Greenberg, M. E. (1999) Cellular survival: a play in three Akts. *Genes Dev*, 13, 2905-2927.

Datta, S. R., Ranger, A. M., Lin, M. Z., Sturgill, J. F., Ma, Y. C., Cowan, C. W., Dikkes, P., Korsmeyer, S. J. and Greenberg, M. E. (2002) Survival factor-mediated BAD phosphorylation raises the mitochondrial threshold for apoptosis. *Dev Cell*, 3, 631-643.

De Duve, C. and Wattiaux, R. (1966) Functions of lysosomes. *Annu Rev Physiol*, 28, 435-492.

Dhar, S., Bitting, R. L., Rylova, S. N., Jansen, P. J., Lockhart, E., Koeberl, D. D., Amalfitano, A. and Boustany, R. M. (2002) Flupirtine blocks apoptosis in batten patient lymphoblasts and in human postmitotic CLN3- and CLN2-deficient neurons. *Ann Neurol*, 51, 448-466.

Ellert-Miklaszewska, A., Kaminska, B. and Konarska, L. (2005) Cannabinoids down-regulate PI3K/Akt and Erk signalling pathways and activate proapoptotic function of Bad protein. *Cell Signal*, 17, 25-37.

Geraets, R. D., Koh, S., Hastings, M. L., Kielian, T., Pearce, D. A. and Weimer, J. M. (2016) Moving towards effective therapeutic strategies for Neuronal Ceroid Lipofuscinosis. *Orphanet J Rare Dis*, 11, 40.

Ghosh, A., Corbett, G. T., Gonzalez, F. J. and Pahan, K. (2012) Gemfibrozil and fenofibrate, Food and Drug Administration-approved lipid-lowering drugs, up-regulate tripeptidyl-peptidase 1 in brain cells via peroxisome proliferator-activated receptor alpha: implications for late infantile Batten disease therapy. *J Biol Chem*, 287, 38922-38935.

Ghosh, A., Jana, M., Modi, K., Gonzalez, F. J., Sims, K. B., Berry-Kravis, E. and Pahan, K. (2015) Activation of peroxisome proliferator-activated receptor alpha induces lysosomal biogenesis in brain cells: implications for lysosomal storage disorders. *J Biol Chem*, 290, 10309-10324.

Ghosh, A. and Pahan, K. (2012a) Gemfibrozil, a lipid-lowering drug, induces suppressor of cytokine signaling 3 in glial cells: implications for neurodegenerative disorders. *J Biol Chem*, 287, 27189-27203.

Ghosh, A. and Pahan, K. (2012b) Gemfibrozil, a lipid-lowering drug, induces suppressor of cytokine signaling 3 in glial cells: Implications for neurodegenerative disorders. *J Biol Chem*.

Ghosh, A., Roy, A., Liu, X. et al. (2007) Selective inhibition of NF-kappaB activation prevents dopaminergic neuronal loss in a mouse model of Parkinson's disease. *Proc Natl Acad Sci USA*, 104, 18754-18759.

Ghosh, A., Roy, A., Matras, J., Brahmachari, S., Gendelman, H. E. and Pahan, K. (2009) Simvastatin inhibits the activation of p21ras and prevents the loss of dopaminergic neurons in a mouse model of Parkinson's disease. *J Neurosci*, 29, 13543-13556.

Hachiya, Y., Hayashi, M., Kumada, S., Uchiyama, A., Tsuchiya, K. and Kurata, K. (2006) Mechanisms of neurodegeneration in neuronal ceroid-lipofuscinoses. *Acta Neuropathol*, 111, 168-177. Jana, M., Jana, A., Liu, X., Ghosh, S. and Pahan, K. (2007) Involvement of phosphatidylinositol 3-kinase-mediated up-regulation of I kappa B alpha in anti-inflammatory effect of gemfibrozil in microglia. *J Immunol*, 179, 4142-4152.

Jana, M. and Pahan, K. (2012) Gemfibrozil, a lipid lowering drug, inhibits the activation of primary human microglia via peroxisome proliferator-activated receptor beta. *Neurochem Res*, 37, 1718-1729.

Khasnavis, S. and Pahan, K. (2014) Cinnamon treatment upregulates neuroprotective proteins Parkin and DJ-1 and protects dopaminergic neurons in a mouse model of Parkinson's disease. *J Neuroimmune Pharmacol*, 9, 569-581.

Kohan, R., Cismondi, I. A., Oller-Ramirez, A. M., Guelbert, N., Anzolini, T. V., Alonso, G., Mole, S. E., de Kremer, D. R. and de Halac, N. I. (2011) Therapeutic approaches to the challenge of neuronal ceroid lipofuscinoses. *Curr Pharm Biotechnol*, 12, 867-883.

Koyasu, S. (2003) The role of PI3K in immune cells. *Nat Immunol*, 4, 313-319.

Lane, S. C., Jolly, R. D., Schmechel, D. E., Alroy, J. and Boustany, R. M. (1996) Apoptosis as the mechanism of neurodegeneration in Batten's disease. *J Neurochem*, 67, 677-683.

Li, Y., Tennekoon, G. I., Birnbaum, M., Marchionni, M. A. and Rutkowski, J. L. (2001) Neuregulin signaling through a PI3K/Akt/Bad pathway in Schwann cell survival. *Mol Cell Neurosci*, 17, 761-767.

Macauley, S. L., Wong, A. M., Shyng, C. et al. (2014) An anti-neuroinflammatory that targets dysregulated glia enhances the efficacy of CNS-directed gene therapy in murine infantile neuronal ceroid lipofuscinosis. *J Neurosci,* 34, 13077-13082.

Otvos, J. D., Collins, D., Freedman, D. S., Shalaurova, I., Schaefer, E. J., McNamara, J. R., Bloomfield, H. E. and Robins, S. J. (2006) Low-density lipoprotein and high-density lipoprotein particle subclasses predict coronary events and are favorably changed by gemfibrozil therapy in the Veterans Affairs High-Density Lipoprotein Intervention Trial. *Circulation,* 113, 1556-1563.

Pahan, K. (2006) Lipid-lowering drugs. *Cell Mol Life Sci,* 63, 1165-1178.

Pahan, K., Jana, M., Liu, X., Taylor, B. S., Wood, C. and Fischer, S. M. (2002) Gemfibrozil, a lipid lowering drug, inhibits the induction of nitric-oxide synthase in human astrocytes. *J Biol Chem,* 277, 45984-45991.

Perez-Sala, D., Boya, P., Ramos, I., Herrera, M. and Stamatakis, K. (2009) The C-terminal sequence of RhoB directs protein degradation through an endo-lysosomal pathway. *PLoS One,* 4, e8117.

Puranam, K., Qian, W. H., Nikbakht, K., Venable, M., Obeid, L., Hannun, Y. and Boustany, R. M. (1997) Upregulation of Bcl-2 and elevation of ceramide in Batten disease. *Neuropediatrics,* 28, 37-41.

Robins, S. J., Collins, D., Wittes, J. T. et al. (2001) Relation of gemfibrozil treatment and lipid levels with major coronary events: VA-HIT: a randomized controlled trial. *JAMA,* 285, 1585-1591.

Roy, A., Jana, M., Kundu, M., Corbett, G. T., Rangaswamy, S. B., Mishra, R. K., Luan, C. H., Gonzalez, F. J. and Pahan, K. (2015) HMG-CoA Reductase Inhibitors Bind to PPARalpha to Upregulate Neurotrophin Expression in the Brain and Improve Memory in Mice. *Cell Metab,* 22, 253-265.

Roy, A., Kundu, M., Jana, M., Mishra, R. K., Yung, Y., Luan, C. H., Gonzalez, F. J. and Pahan, K. (2016) Identification and characterization of PPARalpha ligands in the hippocampus. *Nat Chem Biol,* 12, 1075-1083.

Roy, A. and Pahan, K. (2009) Gemfibrozil, stretching arms beyond lipid lowering. *Immunopharmacol Immunotoxicol,* 31, 339-351.

Rubins, H. B. and Robins, S. J. (1992) Effect of reduction of plasma triglycerides with gemfibrozil on high-density-lipoprotein-cholesterol concentrations. *J Intern Med,* 231, 421-426.

Rubins, H. B., Robins, S. J., Collins, D. et al. (1999) Gemfibrozil for the secondary prevention of coronary heart disease in men with low levels of high-density lipoprotein cholesterol. Veterans Affairs High-Density Lipoprotein Cholesterol Intervention Trial Study Group. *N Engl J Med,* 341, 410-418.

Saha, R. N. and Pahan, K. (2006) HATs and HDACs in neurodegeneration: a tale of disconcerted acetylation homeostasis. *Cell Death Differ,* 13, 539-550.

Shyng, C. and Sands, M. S. (2014) Astrocytosis in infantile neuronal ceroid lipofuscinosis: friend or foe? *Biochem Soc Trans,* 42, 1282-1285.

Sleat, D. E., Donnelly, R. J., Lackland, H., Liu, C. G., Sohar, I., Pullarkat, R. K. and Lobel, P. (1997) Association of mutations in a lysosomal protein with classical late-infantile neuronal ceroid lipofuscinosis. *Science,* 277, 1802-1805.

Sleat, D. E., El-Banna, M., Sohar, I., Kim, K. H., Dobrenis, K., Walkley, S. U. and Lobel, P. (2008) Residual levels of tripeptidyl-peptidase I activity dramatically ameliorate disease in late infantile neuronal ceroid lipofuscinosis. *Mol Genet Metab,* 94, 222-233.

Sleat, D. E., Wiseman, J. A., El-Banna, M. et al. (2004) A mouse model of classical late-infantile neuronal ceroid lipofuscinosis based on targeted disruption of the CLN2 gene results in a loss of tripeptidyl-peptidase I activity and progressive neurodegeneration. *J Neurosci,* 24, 9117-9126.

Smalley, C. M. and Goldberg, S. J. (2008) A pilot study in the efficacy and safety of gemfibrozil in a pediatric population. *J Clin Lipidol,* 2, 106-111.

Sohar, I., Sleat, D. E., Jadot, M. and Lobel, P. (1999) Biochemical characterization of a lysosomal protease deficient in classical late infantile neuronal ceroid lipofuscinosis (LINCL) and development of an enzyme-based assay for diagnosis and exclusion of LINCL in human specimens and animal models. *J Neurochem,* 73, 700-711.

Superko, H. R., Berneis, K. K., Williams, P. T., Rizzo, M. and Wood, P. D. (2005) Gemfibrozil reduces small low-density lipoprotein more in normolipemic subjects classified as low-density lipoprotein pattern B compared with pattern A. *Am J Cardiol,* 96, 1266-1272.

Walus, M., Kida, E. and Golabek, A. A. (2010) Functional consequences and rescue potential of pathogenic missense mutations in tripeptidyl peptidase I. *Hum Mutat,* 31, 710-721.

The invention claimed is:

1. A method of decreasing neuronal apotopic cell death in a subject having neuronal ceroid lipofuscinosis, the method comprising administering to the subject a composition comprising a therapeutically effective amount of gemfibrozil to decrease neuronal apoptotic cell death of the subject having the neuronal ceroid lipofuscinosis relative to a control not receiving gemfibrozil.

2. The method according to claim 1, wherein the neuronal ceroid lipofuscinosis is Late Infantile Neuronal Ceroid Lipofuscinosis.

3. The method according to claim 1, wherein the gemfibrozil increases a level of phospho-BCL2 Associated Agonist Of Cell Death (P-BAD) in the subject.

4. The method according to claim 3, wherein the level of P-BAD is increased in a motor cortex or a striatum of the subject.

5. A method of prolonging a lifespan of a subject having neuronal ceroid lipofuscinosis, the method comprising administering to the subject a composition comprising a therapeutically effective amount of gemfibrozil to prolong the lifespan of the subject having neuronal ceroid lipofuscinosis relative to a control not receiving gemfibrozil.

6. The method according to claim 5, wherein the neuronal ceroid lipofuscinosis is Late Infantile Neuronal Ceroid Lipofuscinosis.

7. A method of improving motor behavior of a subject having neuronal ceroid lipofuscinosis, the method comprising administering to the subject a composition comprising a therapeutically effective amount of gemfibrozil to improve motor behavior of the subject having neuronal ceroid lipofuscinosis relative to a control not receiving.

8. The method according to claim 7, the neuronal ceroid lipofuscinosis is Late Infantile Neuronal Ceroid Lipofuscinosis.

9. A method of increasing levels of anti-inflammatory factors in a brain of a subject having late infantile neuronal ceroid lipofuscinosis, the method comprising administering to the subject a composition comprising a therapeutically effective amount of gemfibrozil to increase levels of anti-inflammatory factors in a brain of the subject having the Late Infantile Neuronal Ceroid Lipofuscinosis relative to a control not receiving gemfibrozil.

10. The method according to claim 5, wherein the gemfibrozil increases a level of phospho-BCL2 Associated Agonist Of Cell Death (P-BAD) in the subject.

11. The method according to claim 10, wherein the level of P-BAD is increased in a motor cortex or a striatum of the subject.

12. The method according to claim 7, wherein the gemfibrozil increases a level of phospho-BCL2 Associated Agonist Of Cell Death (P-BAD) in the subject.

13. The method according to claim 12, wherein the level of P-BAD is increased in a motor cortex or a striatum of the subject.

14. The method according to claim 9, wherein the gemfibrozil increases a level of phospho-BCL2 Associated Agonist Of Cell Death (P-BAD) in the subject.

15. The method according to claim 14, wherein the level of P-BAD is increased in a motor cortex or a striatum of the subject.

\* \* \* \* \*